United States Patent [19]

Karpiak

[11] Patent Number: 5,195,987
[45] Date of Patent: Mar. 23, 1993

[54] EMERGENCY I.V. SET-UP APPARATUS

[76] Inventor: Kenneth D. Karpiak, 2286B Levante St., Carlsbad, Calif. 92009

[21] Appl. No.: 745,919

[22] Filed: Aug. 16, 1991

[51] Int. Cl.$^5$ ............................................. A61M 5/00
[52] U.S. Cl. .................................. 604/262; 604/257; 604/408
[58] Field of Search .................. 604/49, 51-53, 604/80, 257, 259, 261-262, 408-410; 206/364, 570-571

[56] References Cited

U.S. PATENT DOCUMENTS

| | | | |
|---|---|---|---|
| 2,866,457 | 12/1958 | Moore | 604/251 X |
| 2,999,499 | 9/1961 | Willet | 604/251 X |
| 3,473,532 | 10/1969 | Eisenberg | 604/262 |
| 3,724,461 | 4/1973 | Eisenberg | 604/262 |
| 4,248,223 | 2/1981 | Turner et al. | 604/251 X |
| 4,548,600 | 10/1985 | Ruschke | 604/122 |
| 4,573,980 | 3/1986 | Karrasch et al. | 604/256 |
| 4,781,698 | 11/1988 | Parren | 604/246 |

FOREIGN PATENT DOCUMENTS

| | | | |
|---|---|---|---|
| 1188661 | 9/1959 | France | 604/262 |
| 586321 | 12/1958 | Italy | 604/408 |
| 1264652 | 2/1972 | United Kingdom | 604/408 |

Primary Examiner—C. Fred Rosenbaum
Assistant Examiner—C. Maglione
Attorney, Agent, or Firm—David J. Harshman

[57] ABSTRACT

Emergency I.V. set-up apparatus comprises a flexible bag and flexible tube fixedly attached to the bag, and pre-packaged in one sterile package. The apparatus includes a base to which a cap is securely attached, with an output end of the flexible tube inserted into the cap in a sterile manner to block off the I.V. tube. A valve is connected to the tubing to control flow from the bag into the tubing. The bag and tube, may be pre-filled and pre-primed. In operation, an emergency field personnel paramedic can remove the flexible tube with one hand to begin an I.V. solution delivery to a patient alone in a very small amount of time.

9 Claims, 1 Drawing Sheet

EMERGENCY I.V. SET-UP APPARATUS

FIELD OF THE INVENTION

This invention relates generally to medical apparatus for delivering intravenous (I.V.) solutions to a patient. More specifically, the invention relates to an emergency I.V. set-up apparatus for establishing a flow of intravenous solution into the vein of a patient. The present invention is particularly, though not exclusively, useful for setting up the delivery of intravenous solutions to a patient in an emergency situation in the field by trained personnel such as paramedics.

BACKGROUND OF THE INVENTION

In the past, there have been many different types of medical devices for containing and delivering medicinal solutions into the veins of a patient. Such devices typically include a flexible container or bag which holds the particular I.V. solution to be delivered to the patient. The I.V. bag is typically sealed with the solution inside the bag in a sterile environment. The I.V. bag may include one or two ports for allowing release of the I.V. solution. Flexible tubing is typically provided which has one end connectable to the port on the I.V. bag, and the other end connectable to an I.V. catheter pre-inserted into a patient. There may be valves associated with the tube and various mechanisms for controlling the flow into the patient. Typically the bag tubing and any extension tubing that are used also must be subjected to sterile packaging and conditions for proper use.

Over the years, various devices for delivering I.V. solutions have included such devices as the Parenteral fluid container and closure assembly as disclosed in U.S. Pat. No. 3,209,752, to Bujan, et al. This discloses a protective closure assembly for the tubular portion of the apparatus.

Another device is that disclosed in U.S. Pat. No. 4,687,473 to Raines for a self-contained secondary solution set. This discloses a self-contained I.V. set for infusing drugs having a mini I.V. container with a filtered air vent and valve filling port which uses a disposable syringe. A drip chamber below the mini I.V. container receives medication through a drip device at the bottom of the container.

Another device is that disclosed in U.S. Pat. No. 4,722,727 to Ogden, et al. for a flexible I.V. container. This discloses a piece of flexible tubing which is used to connect with other tubings in an I.V. fluid system.

With each of the above-mentioned devices, and with all devices in this field pertaining to intravenous solutions, it is critical that the particular apparatus for delivering the I.V. solution to the patient establish and maintain sterile conditions to ensure no foreign bacterial or viruses get into the system, and consequently into the patient's veins. Thus, such apparatus typically come prepackaged in sterile packages or containers, i.e., the tubing comes in a sterile container, and each end of the tube is covered with a cap or other mechanism for maintaining sterile conditions.

In an emergency situation, such as that encountered by paramedics in caring for patients found at traumatic situations in the field, time is very precious. In particular, a delay of just a few seconds in establishing advanced life support services, and an I.V. for quick volume replacement with the proper medicated solution in particular, can mean the difference between life and death. In addition to the time factor, is the human resource factor, i.e., a sufficient number of qualified personnel to deliver the medical services for the field emergency situation at hand. Many times in field emergency situations, especially when there is more than one patient at a scene, allocation of personnel among patients could be crucial. In particular, with respect to establishing an I.V., use of current methods and procedures as known in the prior art typically requires two individuals to establish the I.V. connection with the patient in a short period of time. For example, conventional I.V. bags are packed in a sterile package, and a conventional I.V. tubing kit is also packed in a conventional package. The I.V. tubing kit includes a valve on one end which can be inserted into a port on the conventional I.V. bag, and a cap on the other end. In addition, extension tubing is packaged in another, third, separate bag in a sterile fashion.

Once the emergency personnel or paramedics arrive on the scene with the proper equipment and have made the proper diagnosis, and have elected to start an I.V. solution, begin to assemble the various components. The I.V. bag opens from the package and removed, and the tubing is removed from the sterile package. One end of the tubing is inserted into a port of the I.V. bag and a connection is made. Once the I.V. bag, tubing, and extension tubing, have been assembled, they must also be primed, in other words the fluid from the bag must be introduced into the tube and remove any air bubbles in the line so as to prevent any air bubbles from going into the patient, with the line then being full of the I.V. solution fluid. This assembly operation of the various components requires two hands of the person putting the I.V. bag and flexible tube together. The same or another individual medically-trained staff, such as paramedic must introduce a needle/catheter into the vein of the patient, which requires both hands for insertion, and after insertion at least one hand to hold the vein immediately proximal to the I.V. needle to prevent blood from squirting out of the open I.V. catheter to which the tubing has not yet been connected.

It may readily be seen that the assembly procedure for connecting the flexible tubing, and any extension ports, to the I.V. fluid bag, while maintaining necessary sterile conditions, requires both hands of at least one person. If the scene of the trauma with the patient is such that only one medical professional can complete both steps of (i) assembling the bag, tubing, and extension tubing, and priming the system, and (ii) inserting the needle/catheter into the vein of the patient which is then ready for the primed I.V. tubing to be connected. The total time before the fluid can be introduced into the patient is thus the total time of the first step plus the total time of the second step. As an alternative, steps (i) and (ii) can be accomplished in a quick fashion by two individuals accomplishing each separate task simultaneously. While this reduces the amount of time required, it can readily be seen that it requires two individuals to accomplish it. Thus it can readily be seen that in situations where time for delivery of the solution is critical, if there is only one individual available the time to establish the I.V. by one person doing the entire task will be increased, which increase in time can mean death to the patient.

Accordingly, it is an object of the present invention to provide an emergency I.V. set-up apparatus which allows an I.V. solution connection be established with a patient in a very short period of time.

It is yet another object of the present invention to provide an emergency I.V. set-up apparatus constructed to accommodate establishment of an I.V. solution connection to a patient in a short period of time by one person.

Still another object of the present invention is to provide an emergency I.V. set-up apparatus which is durable in construction and reliable in operation.

Yet another object of the present invention is to provide a emergency I.V. set-up apparatus which is simple and convenient to use.

SUMMARY OF THE INVENTION

A preferred embodiment of the emergency I.V. set-up apparatus includes a flexible bag for containing I.V. fluid is connected to in fluid communication with a flexible I.V. tube and extension tubing in one sterile package. The extension tubing has a sterile outlet end which is inserted into a cap. The cap is fixedly connected to the container to permit the outlet end of the tube to be removed from the cap by pulling on the tube. The container and tubing are pre-filled with I.V. fluid, and the tube is pre-primed. An I.V. drip chamber is connected between the tubing and container. Between the drip chamber and the bag, there is an on/off valve. The tube includes medication injection ports and extension tubing. Since the apparatus is an integral unit, which is ready for use, it can be immediately removed from its sterile container, and the tube removed from the cap with one hand by an emergency medical professional such as a paramedic for starting an I.V. in a patient in less time and without assistance.

The novel features of this invention, as well as the invention itself, both as to its structure and its operation, will be best understood from the accompanying drawings taken in conjunction with the accompanying descriptions in which similar reference characters refer to similar parts and in which:

DESCRIPTION OF THE PREFERRED EMBODIMENT

Figure 1:
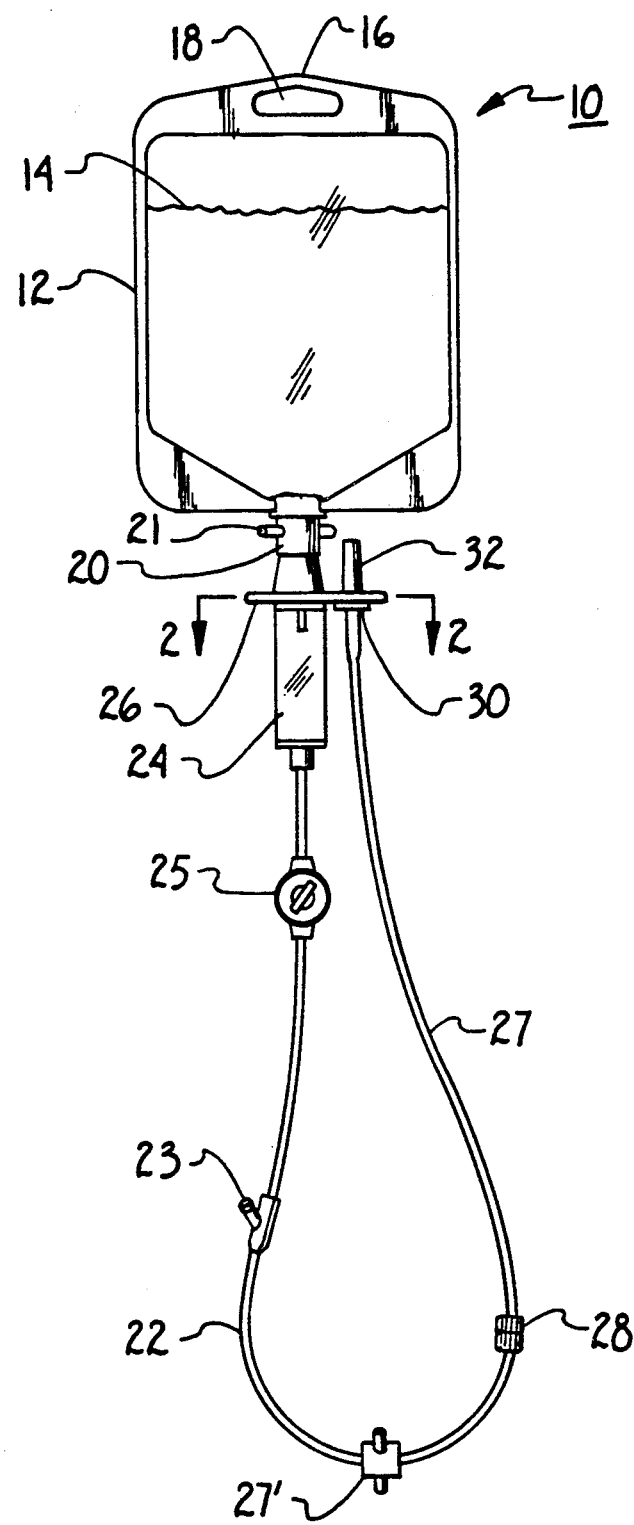
FIG. 1 is a perspective front view of the emergency I.V. set-up apparatus in accordance with the present invention.

Referring now to FIG. 1 there is shown an emergency I.V. set-up apparatus 10 in accordance with the present invention, which is pre-assembled in one sterile package. Apparatus 10 comprises flexible container or bag 12 which contains liquid I.V. solution 14. I.V. solution 14 can be any preferred, pre-hospital I.V. solution for delivery to a patient for volume replacement. The top of bag 12 includes a support member 16 for extending bag 14 in a desired elevated position. In the embodiment shown, support member 16 comprises a loop having a hole 18 for an end of the apparatus end to be hung on a hook or other convenient protrusion for suspending the apparatus in a desired elevation. The bottom of bag 12 has an outlet port 20 for releasing the I.V. fluid 14. Outlet port 20 includes on/off valve 21 which is in a normally closed position when packaged, which can be fully opened for use. Outlet port 20 is in fluid communication with a flexible I.V. tube 22. In the embodiment shown, connected between outlet port 20 and I.V. tube 22 is a drip chamber 24. Drip chamber 24 is a conventional drip chamber which includes a flexible, resilient portion which when squeezed pushes air into the bag to displace fluid from bag 12 through port 20 through open valve 21 into flexible tube 22 when the apparatus is being used.

Drip chamber 24 includes a rigid base plate 26 which provides structural support for drip chamber 24. Flexible tube 22 in the embodiment shown includes medical injection ports 23 which are connected in fluid communication with flexible tube 22 allow medication to be introduced into flexible tube 22 for delivery out its outlet end 30. Also included is a drip rate adjustment mechanism 25 to adjust flow rate, and on/off valve 27' to shut off flow distal to drip chamber 24. End of tubing 22 is removably pre-connected to extension tubing portion 27 at connection 28. Outlet end 30 of extension tubing 27 is inserted in and covered by cap 32, which cap 32 is permanently connected to base plate 26 of drip chamber 24. The details of the cap 32 can perhaps best be appreciated further with reference to FIGS. 2 and 3.

Figure 2:
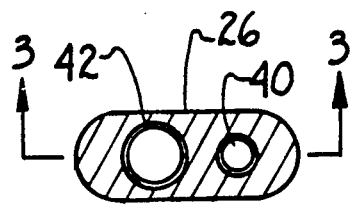
FIG. 2 is a top cross-sectional view of the apparatus taken along line 2—2 of FIG. 1.
Figure 3:
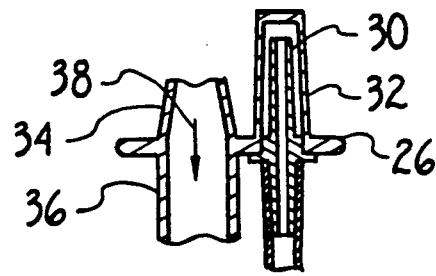
FIG. 3 is a side cross-sectional view of a portion of the apparatus showing the attachment of the cap taken along line 3—3 of FIG. 2.

There is shown in FIG. 2 and 3 the fluid connection between upper portion 34 and lower portion 36 of drip chamber 24. The flow of fluid 12 is illustrated by arrow 38. In addition, it can be seen how cap 32 is attached to base plate 26, where outlet end 30 of flexible tubing 27 has been pre-inserted into cap 32 in a sterile condition. The sterile condition is maintained since cap 32 is fixedly connected to base 26 and is not removable therefrom.

In one embodiment, valve 21, is closed. In another embodiment, valve 21 is open, and fluid 12 is also present in flexible tubes 22 and 27, and the system is pre-primed when it is packaged in a sterile condition for readily available use by the appropriate medical personnel. It can be seen that flexible tube 22, and outlet end 30 of tube 27 can extend through baseplate 26 at hole 40, and fluid 12 passes through baseplate 26 through hole 42 in baseplate 26.

Figure 4:
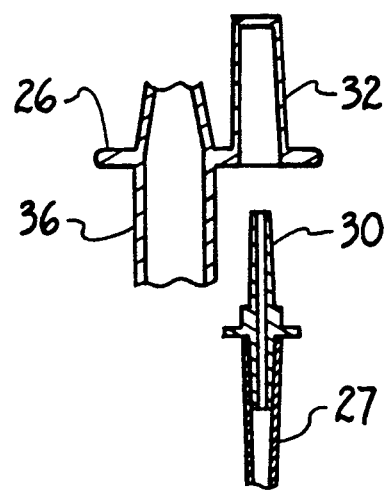
FIG. 4 is a cross-sectional view of the portion of the apparatus as shown in FIG. 3, with the tube removed from the cap.

The operation of the apparatus can perhaps best be appreciated with reference to FIG. 4, in which it can readily be seen that by grasping flexible extension tube 27 and pulling on it, outlet end 30 is released from cap 32. In one embodiment, when valve 21 is closed when apparatus 10 is packaged, and there is no fluid in tube 22 and 27, the paramedic hangs the bag, opens the valve 21, and removes end 30 from cap 32, and uses drip chamber 24 to prime the system, reinserting end 30 into cap 32. Outlet end 30 is then ready to be connected to an I.V. catheter (not shown) which has already been inserted into the patient's body. It is crucial to note that since the cap 32 is connected to baseplate 26, and it is assumed that bag 12 is supported in some fashion, the medical practitioner or paramedic can use one hand to pull flexible tube 22 and release it so it is ready to insert it into the catheter, since the system is primed. In another embodiment, in which valve 21 is open when packaged, the tubes 22 and 27 are filled and pre-primed when shipped. In either embodiment, in a life or death situation, the benefits of the present invention can be realized in order to allow one paramedic to use the system in a very fast and efficient manner to help a patient, especially in situations of emergency in which a few moments can be critical.

While the particular emergency I.V. set-up apparatus as herein shown and disclosed in detail is fully capable of obtaining the object and providing the advantages hereinbefore stated, it is to be understood that it is merely illustrative of the presently-preferred embodiment of the invention, and that no limitations are intended of the details of construction or design herein shown other than as defined in the appended claims.

What is claimed is:

1. An emergency I.V. set-up apparatus, comprising:
    a flexible container for containing I.V. fluid having means for hanging said container;
    a flexible tube fixedly connected in fluid communication with said container, said tube having a sterile outlet end;
    a drip chamber connected to said tube, said drip chamber having a rigid base;
    a cap for covering said sterile outlet end, said cap being fixedly connected to said rigid base to permit said sterile outlet end of said tube to be removed from said cap by pulling on said tube.

2. The apparatus of claim 1, wherein said tubing includes extension tubing.

3. The apparatus as in claim 2, further comprising a valve connected to said tubing.

4. The apparatus of claim 3, further comprising medication injection ports in said tube.

5. The apparatus as in claim 1, further comprising a drip chamber mechanism connected in fluid communication between said container and said tube.

6. The apparatus as in claim 5, wherein said container and tube are pre-filled with I.V. fluid.

7. Apparatus as in claim 6, wherein said tube is pre-primed.

8. A method of establishing an emergency I.V. set up comprising the steps of:
    providing a flexible container having a flexible tube fixedly attached thereto, a drip chamber and connected to said tube having a rigid base connected thereto; and a cap pre-attached to the base, with one end of the flexible tube inserted into the cap;
    suspending the bag at a desired elevation;
    grasping said tube and pulling said tube from said cap while said cap remains fixed to said base for releasing an outlet of said tube; and
    connecting said outlet end of said tube in fluid communication with an intravenous catheter inserted in the body of a patient.

9. The method of claim 8, further comprising:
    providing a valve attached to said tubing;
    opening said valve to permit fluid to flow into said tubing; and
    priming said tubing.

* * * * *